US012630783B2

(12) United States Patent
Chandrasekaran et al.

(10) Patent No.: US 12,630,783 B2
(45) Date of Patent: May 19, 2026

(54) MUGUET TYPE FRAGRANCE COMPOUNDS

(71) Applicant: SYMRISE AG, Holzminden (DE)

(72) Inventors: Vijayanand Chandrasekaran, Holzminden (DE); Bernd Hölscher, Halle (DE)

(73) Assignee: SYMRISE AG, Holzminden (DE)

( * ) Notice: Subject to any disclaimer, the term of this patent is extended or adjusted under 35 U.S.C. 154(b) by 572 days.

(21) Appl. No.: 18/245,238

(22) PCT Filed: Sep. 18, 2020

(86) PCT No.: PCT/EP2020/076153
§ 371 (c)(1),
(2) Date: Mar. 14, 2023

(87) PCT Pub. No.: WO2022/058019
PCT Pub. Date: Mar. 24, 2022

(65) Prior Publication Data

US 2023/0357664 A1 Nov. 9, 2023

(51) Int. Cl.

| | |
|---|---|
| ***C11B 9/00*** | (2006.01) |
| ***C07C 41/28*** | (2006.01) |
| ***C07C 45/00*** | (2006.01) |
| ***C07C 45/64*** | (2006.01) |
| ***C07C 47/225*** | (2006.01) |

(52) U.S. Cl.
CPC ............ *C11B 9/0034* (2013.01); *C07C 41/28* (2013.01); *C07C 45/00* (2013.01); *C07C 45/64* (2013.01); *C07C 47/225* (2013.01); *C07C 2601/14* (2017.05)

(58) Field of Classification Search
CPC .......... C11B 9/00; C07C 41/28; C07C 45/00; C07C 45/64; C07C 47/225
USPC ........................................................ 512/22, 1
See application file for complete search history.

(56) References Cited

U.S. PATENT DOCUMENTS

2021/0395641 A1* 12/2021 Hölscher ............... C11B 9/0034

FOREIGN PATENT DOCUMENTS

| | | | | |
|---|---|---|---|---|
| EP | 1054053 A2 | 11/2000 | | |
| JP | S59204115 A | 11/1984 | | |
| JP | 2018530646 A | 10/2018 | | |
| JP | 2020514332 A | 5/2020 | | |
| JP | 2023511005 A | 3/2023 | | |
| JP | 2023538721 A | 9/2023 | | |
| WO | 2014180945 A1 | 6/2014 | | |
| WO | 2016074695 A1 | 5/2016 | | |
| WO | 2017046071 A1 | 3/2017 | | |
| WO | 2018167200 A1 | 9/2018 | | |
| WO | WO-2020098923 A1 * | 5/2020 | ............. | C07C 47/11 |
| WO | 2021148491 A1 | 7/2021 | | |
| WO | 2022049036 A2 | 3/2022 | | |

OTHER PUBLICATIONS

Indian Office Action issued on Sep. 12, 2023 for corresponding Indian Application No. 202237054278.
Article: "Acetal" https://en.wikipedia.org/wiki/Acet al.
International Search Report and Written Opinion issued on Jun. 15, 2021 for corresponding PCT Application No. PCT/EP2020/076153.
Database Regisrty [Online] Chemical Abstracts Service, Columbus, Ohio, US; "6-methylene-1-cyclohexene-1-propanal", 2014 XP002803194.
English translation of the Japanese Office Action issued on Aug. 26, 2024 for corresponding Japanese Application No. 2022-570690.
Registry (STN) [online], 2015, [retrieved Aug. 16, 2024.], CAS registration Nos. 60210-93-7, 60416-25-3, 99128-28-6, 111772-48-6, 663603-28-9, 1449040-09-8, 1823092-09-6.

* cited by examiner

*Primary Examiner* — Jessica Whiteley
(74) *Attorney, Agent, or Firm* — POLSINELLI PC

(57) ABSTRACT

The present invention primarily relates to compounds of formula (I) as defined herein and to compositions comprising one, two, three or more compounds of formula (I) as defined herein, or consisting of two, three or more compounds of formula (I) as defined herein. The invention further relates to methods for producing compounds of formula (I) (or (Ia) or (Ib)), to the use of compounds of formula (I) as fragrance substances and the use of compositions comprising a compound of formula (I) or consisting of compounds of formula (I) as fragrance substance mixtures. It further relates to fragrance substance compositions comprising or consisting of compounds or compositions as defined herein and one or more additional fragrance substances, to perfumed products comprising compounds or compositions or fragrance substance compositions as defined herein, to methods for producing perfumed products as defined herein and to methods for perfuming hair, skin, textile fibres, surfaces and/or ambient air.

15 Claims, No Drawings

MUGUET TYPE FRAGRANCE COMPOUNDS

CROSS-REFERENCE TO RELATED APPLICATIONS

This application is a national stage application (under 35 U.S.C. § 371) of PCT/EP2020/076153, filed Sep. 18, 2020, which is incorporated herein by reference in its entirety.

The present invention primarily relates to compounds of formula (I) as defined herein and to compositions comprising one, two, three or more compounds of formula (I) as defined herein, or consisting of two, three or more compounds of formula (I) as defined herein. The invention further relates to methods for producing compounds of formula (I) (or (Ia) or (Ib)), to the use of compounds of formula (I) as fragrance substances and the use of compositions comprising a compound of formula (I) or consisting of compounds of formula (I) as fragrance substance mixtures. It further relates to fragrance substance compositions comprising or consisting of compounds or compositions as defined herein and one or more additional fragrance substances, to perfumed products comprising compounds or compositions or fragrance substance compositions as defined herein, to methods for producing perfumed products as defined herein and to methods for perfuming hair, skin, textile fibres, surfaces and/or ambient air.

Further aspects and preferred embodiments of the present invention result from the following explanations, the attached examples and, in particular, the attached patent claims.

Despite a large number of existing fragrance substances, there is still a general need for new fragrance substances in the perfume industry. For example, there is a need for fragrance substances that are capable (in fragrance substance compositions) of producing not only a primary olfactory note but also further interesting notes and of expanding the possibilities of the perfumer with their novel or inventive olfactory properties. In particular, compounds with a floral and/or fruity olfactory note are an indispensable component in the perfume industry and in the production of cosmetics, body care products and washing and cleaning products. An especially valuable class of these fragrances are compounds with an olfactory note of lily of the valley (also called muguet).

The search for suitable substances that led to the present invention was complicated by the following facts:

- The mechanisms of olfactory perception are not sufficiently known;
- the connections between the specific olfactory perception on the one hand and the chemical structure of the associated fragrance substance on the other hand have not been sufficiently researched;
- often even minor changes in the structural set-up of a known fragrance substance cause major changes in the sensory properties and affect the tolerance for the human organism.

The primary object was to find fragrance substances that have an interesting, preferably complex, and inventive sensory profile and are suitable as fragrance substances for use in perfumery.

The sought-after substances should enable the production of novel fragrance substance compositions with special olfactory notes and aspects. Substances which are particularly suitable for combination with other fragrance substances would be advantageous.

In addition, fragrance substances fulfilling this primary object should preferably have additional positive secondary properties in addition to their primary, i.e. olfactory, properties, such as e.g. high stability under certain application conditions, high yield, good adhesion, high substantivity or odour enhancing properties (so-called booster or enhancer effect) and/or, in combination with other fragrance substances, round off their naturalness, freshness, fullness, (radiant) power and/or radiance so that remarkable sensory effects can be achieved.

The primary assigned object is solved according the invention by a compound of formula (I)

(I)

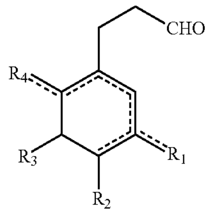

wherein

- $R_1$ represents H, methyl, isopropyl or $=CH_2$, and
- $R_2$ represents H, and
- $R_3$ represents H, isopropyl or isobutyl, and
- $R_4$ represents H or $=CH_2$, wherein the compound of formula (I) comprises either one or two double bond(s) in the area indicated by the dashed line and the remaining bonds represent single bonds.

The compounds of formula (I) have their own unique olfactory properties, which stand out from and exceed those of the known fragrance substances. In particular, they have an (inherent) lily of the valley, aldehydic, bourgeonal and/or floral odour.

The suitability of the compounds of formula (I) as fragrance substances was not known to date. It is therefore particularly surprising that fragrance substances with valuable, interesting and complex olfactory properties could be found in the already well investigated field.

Preferably, the compound of formula (I) is selected from the group consisting of 3-(5-isopropyl-2-methylene-cyclohexyl)-propanal, 3-(5-isopropyl-3-methyl-cyclohexen-1-yl) propanal, 3-(3-isopropyl-5-methyl-cyclohexen-1-yl)propanal, 3-(5-isobutyl-3-methyl-cyclohexen-1-yl)propanal, 3-(3-isobutyl-5-methyl-cyclohexen-1-yl)propanal, 3-(3-isobutyl-5-methyl-cyclohexa-1,5-dien-1-yl)propanal, 3-(5-isobutyl-3-methyl-cyclohexa-1,3-dien-1-yl)propanal, 3-(5-isobutyl-3-methylenecyclohex-1-en-1-yl)propanal, 3-(5-isopropyl-3-methyl-cyclohexa-1,3-dien-1-yl)propanal, 3-(3-isopropyl-5-methyl-cyclohexa-1,5-dien-1-yl)propanal and 3-(5-isopropyl-3-methylene-cyclohexen-1-yl)propanal.

Preferably, the compound of formula (I) is selected from the group consisting of 3-(5-isopropyl-3-methyl-cyclohexen-1-yl)propanal, 3-(3-isopropyl-5-methyl-cyclohexen-1-yl)propanal, 3-(5-isobutyl-3-methyl-cyclohexen-1-yl)propanal, 3-(3-isobutyl-5-methyl-cyclohexen-1-yl)propanal, 3-(3-isobutyl-5-methyl-cyclohexa-1,5-dien-1-yl)propanal, 3-(5-isobutyl-3-methyl-cyclohexa-1,3-dien-1-yl)propanal, 3-(5-isobutyl-3-methylenecyclohex-1-en-1-yl)propanal, 3-(5-isopropyl-3-methyl-cyclohexa-1,3-dien-1-yl)propanal, 3-(3-isopropyl-5-methyl-cyclohexa-1,5-dien-1-yl)propanal and 3-(5-isopropyl-3-methylene-cyclohexen-1-yl)propanal.

Preferably, the compound of formula (I) is selected from the group consisting of 3-(5-isopropyl-2-methylene-cyclohexyl)propanal, i.e. is 3-(5-isopropyl-2-methylene-cyclohexyl)propanal.

The compounds of formula (I) according to the invention as defined herein can be present in any stereoisomeric form or can be present as any mixture of stereoisomers (e.g. cis/trans-isomer mixture, diastereomer mixture, racemate).

The preferred compounds of formula (I)

(I)

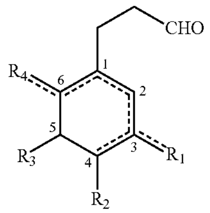

according to the invention as defined herein are described in more detail in the following.

3-(5-Isopropyl-2-methylene-cyclohexyl)propanal is a compound of formula (I), wherein $R_4$ represents $=CH_2$, $R_2$ and $R_3$ represent H, respectively, $R_1$ represents isopropyl and no double bonds are present inside the ring:

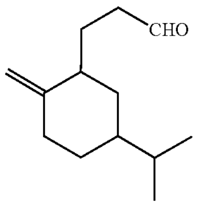

3-(5-Isopropyl-3-methyl-cyclohexen-1-yl)propanal is a compound of formula (I), wherein $R_4$ represents H, $R_3$ represents isopropyl, $R_2$ represents H, $R_1$ represents methyl, the dashed line between C1 and C2 (⎓) represents a double bond and the remaining bonds are single bonds and 3-(3-Isopropyl-5-methyl-cyclohexen-1-yl)propanal is a compound of formula (I), wherein $R_4$ represents H, $R_3$ represents isopropyl, $R_2$ represents H, $R_1$ represents methyl, the dashed line between C6 and C1 (⎓) represents a double bond and the remaining bonds are single bonds. Said two compounds are represented by the following general formula:

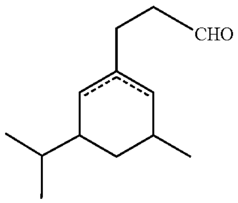

3-(5-Isobutyl-3-methyl-cyclohexen-1-yl)propanal is a compound of formula (I), wherein $R_4$ represents H, $R_3$ represents isobutyl, $R_2$ represents H, $R_1$ represents methyl, the dashed line between C1 and C2 (⎓) represents a double bond and the remaining bonds are single bonds and 3-(3-Isobutyl-5-methyl-cyclohexen-1-yl)propanal is a compound of formula (I), wherein $R_4$ represents H, $R_3$ represents isobutyl, $R_2$ represents H, $R_1$ represents methyl, the dashed line between C6 and 01 (⎓) represents a double bond and the remaining bonds are single bonds. Said two compounds are represented by the following general formula:

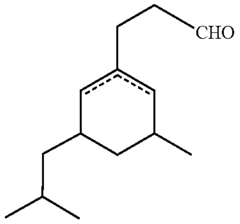

3-(3-Isobutyl-5-methyl-cyclohexa-1,5-dien-1-yl)propanal is a compound of formula (I), wherein $R_4$ represents H, $R_3$ represents isobutyl, $R_2$ represents H, $R_1$ represents methyl, the dashed line (⎓) between C6 and 01 and between C2 and C3 represents a double bond, respectively, and the remaining bonds are single bonds and 3-(5-Isobutyl-3-methyl-cyclohexa-1,3-dien-1-yl)propanal is a compound of formula (I), wherein $R_4$ represents H, $R_3$ represents isobutyl, $R_2$ represents H, $R_1$ represents methyl, the dashed line (⎓) between C1 and C2 and between C3 and C4 represents a double bond, respectively, and the remaining bonds are single bonds and 3-(5-Isobutyl-3-methylenecyclohex-1-en-1-yl)propanal is a compound of formula (I), wherein $R_4$ represents H, $R_3$ represents isobutyl, $R_2$ represents H, $R_1$ represents $=CH_2$, the dashed line between C1 and C2 (⎓) represents a double bond, and the remaining bonds are single bonds. Said three compounds are represented by the following general formula:

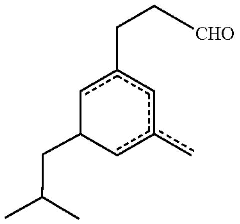

3-(5-Isopropyl-3-methyl-cyclohexa-1,3-dien-1-yl)propanal is a compound of formula (I), wherein $R_4$ represents H, $R_3$ represents isopropyl, $R_2$ represents H, $R_1$ represents methyl, the dashed line (⎓) between 01 and C2 and between C3 and C4 represents a double bond, respectively, and the remaining bonds are single bonds and 3-(3-Isopropyl-5-methyl-cyclohexa-1,5-dien-1-yl)propanal is a compound of formula (I), wherein $R_4$ represents H, $R_3$ represents isopropyl, $R_2$ represents H, $R_1$ represents methyl, the dashed line (⎓) between C6 and 01 and between C2 and C3 represents a double bond, respectively, and the remaining bonds are single bonds and 3-(5-Isopropyl-3-methylene-cyclohexen-1-yl)propanal is a compound of formula (I), wherein $R_4$ represents H, $R_3$ represents isopropyl, $R_2$ represents H, $R_1$ represents $=CH_2$, the dashed line between C1 and C2 (⎓) represents a double bond, and the remaining bonds are single bonds. Said three compounds are represented by the following general formula:

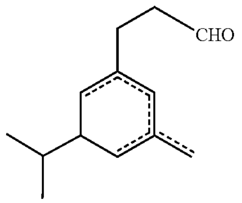

A preferred embodiment of the invention relates to a composition comprising one, two, three or more compounds of formula (I) as defined herein, or consisting of two, three or more compounds of formula (I) as defined herein.

Another aspect of the present invention relates to a method for producing a compound of formula (I)

(I)

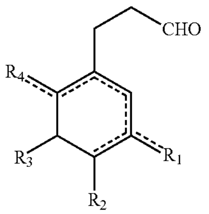

wherein in the compound of formula (I)

$R_1$ represents H, methyl or $=CH_2$, $R_2$ represents H or isopropyl, $R_3$ represents H, isopropyl or isobutyl, $R_4$ represents H, and the compound of formula (I) comprises either one or two double bond(s) in the area indicated by the dashed line and the remaining bonds represent single bonds, and said compound of formula (I) is designated as compound of formula (Ia), comprising or consisting of one, two or more of the following reaction steps:

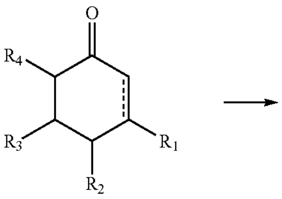

(II)
$R_1$ = H or methyl
$R_2$ = H or isopropyl
$R_3$ = H, isopropyl or isobutyl
$R_4$ = H -continued

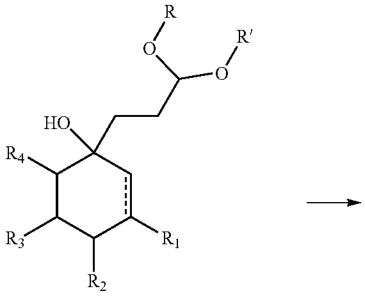

(III)
$R_1$ = H or methyl
$R_2$ = H or isopropyl
$R_3$ = H, isopropyl or isobutyl
$R_4$ = H
R, R′ = independently alkyl or are connected via an alkyl group

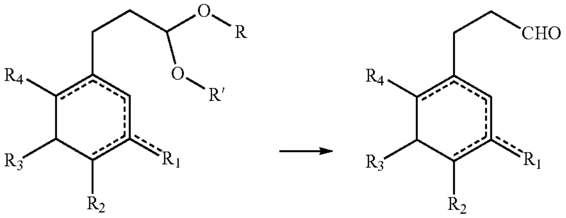

(IV)
$R_1$ = H, or methyl or = $CH_2$
$R_2$ = H or isopropyl
$R_3$ = H, isopropyl or isobutyl
$R_4$ = H
R, R′ = independently alkyl or are connected via an alkyl group (Ia)
$R_1$ = H, or methyl or = $CH_2$
$R_2$ = H or isopropyl
$R_3$ = H, isopropyl or isobutyl
$R_4$ = H wherein in the compounds of formula (II) and (III) the dashed line represents a single or a double bond, respectively, and wherein the compound of formula (IV) comprises either one or two double bond(s) in the area indicated by the dashed line and the remaining bonds represent single bonds.

Hence, said steps of the method as defined herein lead to a compound of formula (Ia)

(Ia)

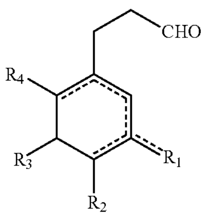

wherein $R_1$ represents H, methyl or $=CH_2$, $R_2$ represents H or isopropyl, $R_3$ represents H, isopropyl or isobutyl, $R_4$ represents H, and wherein the compound of formula (Ia) comprises either one or two double bond(s) in the area indicated by the dashed line and the remaining bonds represent single bonds.

Preferably, in said method according to the invention as defined herein, the compound of formula (II) is reacted with

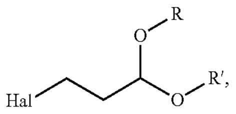

wherein R and R' are independently alkyl, preferably an alkyl residue with 1 to 5 carbon atoms, more preferably methyl, ethyl or propyl, respectively, or may be connected via an alkyl group, preferably ethane-1,2-diyl or propane-1,2-diyl, to form a ring, and Hal is chloride, bromide or iodide, preferably bromide. In a preferred embodiment of this reaction step, compound (II) is reacted with 2-(2-bromoethyl)-1,3-dioxolane (CAS Number 18742-02-4).

Preferably, the alcohol elimination from the compound of formula (III) is carried out with the aid of phosphoryl chloride ($POCl_3$) in pyridine, preferably at a temperature of 0° C. to room temperature.

Preferably, the acetal deprotection of the compound of formula (IV) is carried out with the aid of (concentrated) acid, preferably of concentrated hydrochloric acid (HCl).

According to a preferred embodiment of the method according to the invention, the compound of formula (I) or (Ia) (as produced with the method according to the invention as defined herein) is selected from the group consisting of 3-(5-isopropyl-3-methyl-cyclohexen-1-yl)propanal, 3-(3-isopropyl-5-methyl-cyclohexen-1-yl)propanal, 3-(5-isobutyl-3-methyl-cyclohexen-1-yl)propanal, 3-(3-isobutyl-5-methyl-cyclohexen-1-yl)propanal, 3-(3-isobutyl-5-methyl-cyclohexa-1,5-dien-1-yl)propanal, 3-(5-isobutyl-3-methyl-cyclohexa-1,3-dien-1-yl)propanal, 3-(5-isobutyl-3-methylenecyclohex-1-en-1-yl)propanal, 3-(5-isopropyl-3-methyl-cyclohexa-1,3-dien-1-yl)propanal, 3-(3-isopropyl-5-methyl-cyclohexa-1,5-dien-1-yl)propanal, 3-(5-isopropyl-3-methylene-cyclohexen-1-yl)propanal, and 3-(4-isopropylcyclohexen-1-yl)propanal.

Another aspect of the present invention relates to a method for producing a compound of formula (I)

(I)

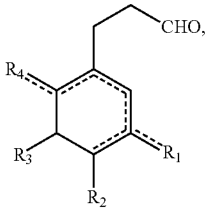

wherein in the compound of formula (I)

$R_1$ represents isopropyl, $R_2$ represents H, $R_3$ represents H, $R_4$ represents $=CH_2$, and each of the remaining dashed lines in the compound of formula (I) represents a single bond, and said compound of formula (I) is designated as compound of formula (Ib), comprising or consisting of one, two or more of the following reaction steps:

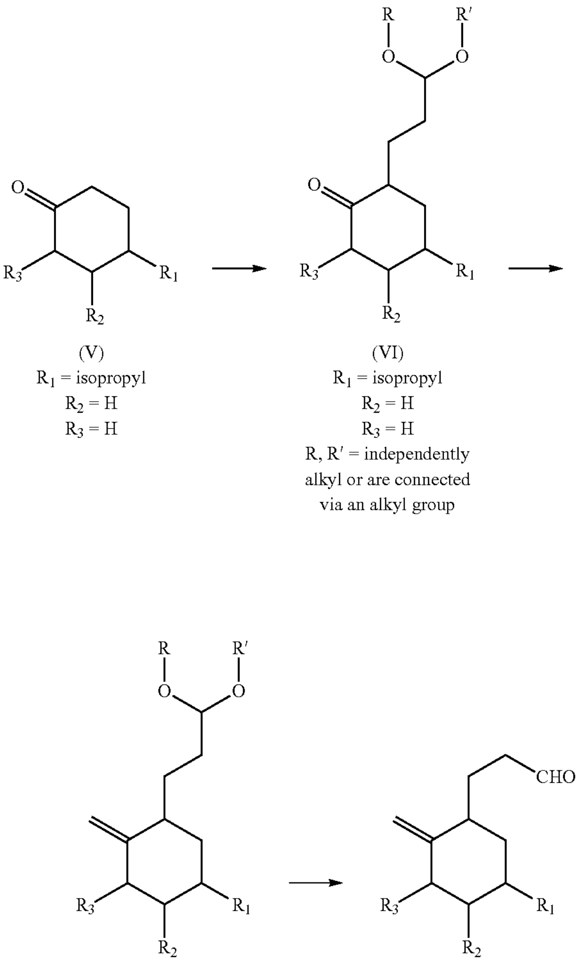

(V)
$R_1$ = isopropyl
$R_2$ = H
$R_3$ = H (VI)
$R_1$ = isopropyl
$R_2$ = H
$R_3$ = H
R, R′ = independently alkyl or are connected via an alkyl group (VII)
$R_1$ = isopropyl
$R_2$ = H
$R_3$ = H
R, R′ = independently alkyl or are connected via an alkyl group (Ib)
$R_1$ = isopropyl
$R_2$ = H
$R_3$ = H Hence, said steps of the method as defined herein lead to a compound of formula (Ib)

(Ib)

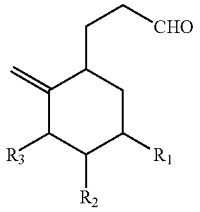

wherein $R_1$ represents isopropyl, $R_2$ represents H, $R_3$ represents H (and $R_4$ as defined in the structure of formula (I) represents $=CH_2$).

Preferably, in said method according to the invention as defined herein, the compound of formula (V) is reacted with

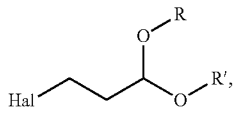

wherein R and R' are independently alkyl, preferably an alkyl residue with 1 to 5 carbon atoms, more preferably methyl, ethyl or propyl, respectively, or may be connected via an alkyl group, preferably ethane-1,2-diyl or propane-1,2-diyl, to form a ring, and Hal is chloride, bromide or iodide, preferably bromide. In a preferred embodiment of this reaction step, compound (V) is reacted with 2-(2-bromoethyl)-1,3-dioxolane (CAS Number 18742-02-4).

Preferably, the conversion of the ketone of the compound of formula (VI) is converted into a carbon-carbon double bond with the aid of methyl(triphenyl)phosphonium bromide and potassium tert-butoxide to give the compound of formula (VII).

Preferably, the acetal deprotection of the compound of formula (VII) is carried out with the aid of (concentrated) acid, preferably of concentrated hydrochloric acid (HCl).

According to a preferred embodiment of the method according to the invention, the compound of formula (I) or (Ib) (as produced with the method according to the invention as defined herein), is selected from the group consisting of 3-(5-isopropyl-2-methylene-cyclohexyl)propanal, i.e. is 3-(5-isopropyl-2-methylene-cyclohexyl)propanal.

Another aspect of the present invention relates to the use of a compound of formula (I) according to the invention as defined herein as a fragrance substance.

In the context of the present text, a fragrance substance is any substance that brings about an olfactory impression, i.e. is suitable for imparting an olfactory impression, or for modifying (enhancing or reducing) the olfactory impression of another (fragrance) substance.

Another aspect of the present invention relates to the use of a composition comprising one, two, three or more compounds of formula (I) as defined herein, or consisting of two, three or more compounds of formula (I) as defined herein as a fragrance substance mixture.

According to a preferred embodiment, the use as defined herein relates to imparting, modifying and/or enhancing one or more olfactory notes selected from the group consisting of the notes green, fatty, ozonic, cyclamen-like, dusty, citrus, mandarin, aldehydic, citral, fresh, lily of the valley, bourgeonal, floral, cucumber, fruity and melon, preferably for imparting, modifying and/or enhancing the olfactory note lily of the valley.

Another aspect of the present invention relates to a fragrance substance composition comprising or consisting of (i) a compound of formula (I) as defined herein, or (ii) a composition comprising one, two, three or more compounds of formula (I) as defined herein, or consisting of two, three or more compounds of formula (I) as defined herein, and one or more additional fragrance substances.

Examples of additional fragrance substances that can be advantageously combined with the compounds of formula (I) as defined herein within the scope of the present invention can be found, for example, in S. Arctander, Perfume and Flavor Materials, Vol. I and II, Montclair, N.J. 1969, Eigenverlag, or K. Bauer et al., Common Fragrance and Flavor Materials, 4th Edition, Wiley-VCH, Weinheim 2001.

To be mentioned in detail: Extracts from natural raw materials such as essential oils, concretes, absolues, resins, resinoids, balsams, tinctures such as ambra tincture; amyris oil; *angelica* seed oil; *angelica* root oil; anise oil; valerian oil; basil oil; tree moss absolute; bay oil; mugwort oil; benzoe resin; bergamot oil; beeswax absolue; birch tar oil; bitter almond oil; savory oil; bucco leaf oil; cabreuva oil; cade oil; calmus oil; camphor oil; *cananga* oil; cardamom oil; cascarilla oil; *cassia* oil; cassie absolue; castoreum absolue; cedar leaf oil; cedar wood oil; cistus oil; citronella oil; lemon oil; copaiba balsam; copaiba balsam oil; coriander oil; costus root oil; cumin oil; cypress oil; davana oil; dill herb oil; dill seed oil; eau de brouts absolue; oak moss absolue; elemi oil; tarragon oil; *eucalyptus citriodora* oil; *eucalyptus* oil; fennel oil; spruce needle oil; *galbanum* oil; *galbanum* resin; geranium oil; grapefruit oil; guaiac wood oil; gurjun balsam; gurjun balsam oil; helichrysum absolue; helichrysum oil; ginger oil; iris root absolue; iris root oil; jasmine absolue; calamus oil; chamomile oil blue; roman chamomile oil; carrot seed oil; cascarilla oil; pine needle oil; spearmint oil; caraway oil; labdanum oil; labdanum absolue; labdanum resin; lavandin absolue; lavandin oil; lavender absolue; lavender oil; lemongrass oil; lovage oil; distilled lime oil; pressed lime oil; linaloe oil; *litsea cubeba* oil; bay leaf oil; macis oil; marjoram oil; mandarin oil; massoi rind oil; *mimosa* absolue; musk seed oil; musk tincture; muscat sage oil; nutmeg oil; myrrh absolue; myrrh oil; myrtle oil; clove leaf oil; clove blossom oil; neroli oil; olibanum absolue; olibanum oil; opopanax oil; orange blossom absolue; orange oil; *origanum* oil; palmarosa oil; patchouli oil; *perilla* oil; Peru balsam oil; parsley leaf oil; parsley seed oil; petit grain oil; peppermint oil; pepper oil; pimento oil; pine oil; poley oil; rose absolue; rosewood oil; rose oil; rosemary oil; sage oil Dalmatian; sage oil Spanish; sandalwood oil; celery seed oil; spiked lavender oil; star anise oil; *styrax* oil; marigold oil; fir needle oil; tea tree oil; turpentine oil; thyme oil; tolu balsam; tonka absolue; tuberose absolute; vanilla extract; violet leaf absolute; *verbena* oil; vetiver oil; juniper berry oil; wine yeast oil; wormwood oil; wintergreen oil; ylang oil; ysop oil; zibet absolue; cinnamon leaf oil; cinnamon bark oil and fractions thereof, or ingredients isolated therefrom.

Moreover, the additional fragrance substances can be fragrance substances from the group of hydrocarbons, such as e.g. 3-carene; α-pinene; β-pinene, α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrene; diphenylmethane;

of aliphatic alcohols such as e.g. hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of aliphatic aldehydes and their acetals such as e.g. hexanel; heptanal; octanel, nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10- trimethyl-9-undecenal; 2,6,10-trimethyl-5,9-undecadienal, heptanaldiethylacetal; 1,1-dimethoxy-2,2,5-trimethyl-4-hexene; citronellyl oxyacetaldehyde; 1-(1-methoxy-propoxy)-(E/Z)-3-hexene;

of aliphatic ketones and their oximes such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

of aliphatic sulphur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles such as e.g. 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of esters of aliphatic carboxylic acids, e.g. (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl crotonate;

of acyclic terpene alcohols such as e.g. geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerates, pentanoates, hexanoates, crotonates, tiglinates and 3-methyl-2-butenoates;

of acyclic terpene aldehydes and ketones such as e.g. citronellal; 7-methoxy-3,7-dimethyloctanal; 2,6,10-trimethyl-9-undecenal; geranylacetone; and the dimethyl and diethyl acetals of geranial, neral;

of cyclic terpene alcohols such as e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerianates, pentanoates, hexanoates, crotonates, tiglinates and 3-methyl-2-butenoates;

of cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethyl-ionone; alpha-iron; beta-damascenone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedrylketone);

of cyclic alcohols such as e.g. 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols such as e.g. alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers such as e.g. cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyldodecahydro-naphtho[2,1-b]furane; 3a-ethyl-6,6,9a-trimethyldodecahydronaphtho[2,1 b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones such as e.g. 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes such as e.g. 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

of cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-Tetramethyl-1,2,3,4,5,6,7,8-octahydro-2-naphtalenylmethylketone; methyl-2,6,10-trimethyl-2,5,9-cyclododecatrienylketone; tert.-butyl-(2,4-dimethyl-3-cyclohexen-1-yl)ketone;

of esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclo-pentylcyclopentylcrotonate; 3-pentyltetrahydro-2H-pyran-4-yl acetate; decahydro-2,5,5,8α-tetramethyl-2-naphthyl acetate; 4,7-methano-3a,4,5,6,7,7a-hexa-hydro-5, or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

of esters of cycloaliphatic alcohols such as e.g. 1-cyclohexylethylcrotonate;

of esters of cycloaliphatic carboxylic acids such as e.g. allyl-3-cyclohexylpropionate; allylcyclohexyloxyacetate; cis- and trans-methyldihydrojasmonate; cis- and trans-methyljasmonate; methyl-2-hexyl-3-oxocyclopentanecarboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

of araliphatic alcohols such as e.g. benzyl alcohol; 1-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids such as e.g. benzylacetate; benzyl propionate; benzyl isobutyrate; benzyl isovalerianate; 2-phenylethyl acetate; 2-phenylethyl propionate; 2-phenylethyl isobutyrate; 2-phenyl ethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

of araliphatic ethers such as e.g. 2-phenylethyl methyl ether; 2-phenylethyl isoamyl ether; 2-phenylethyl-1-ethoxyethyl ether; phenylacetaldehyde dimethylacetal; phenylacetaldehyde diethylacetal; hydratropaaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-isobutylphenyl)propanal; 3-(4-tert.-butyl-phenyl)propanal; cinnamic aldehyde; alpha-butyl cinnamic aldehyde; alpha-hexyl cinnamic aldehyde; 3-methyl-5-phenylpentanal; 4-m ethoxybenzaldehyde; 4-hydroxy-3-methoxybenzaldehyde; 4-Hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones such as e.g. acetophenone; 4-methylacetophenone; 4-methoxyacetophenone; 4-tert.-butyl-2,6-dimethylaceto-phenone; 4-phenyl-2-butanone; 4-(4-hydroxyphenyl)-2-butanone; 1-(2-naphtha-lenyl)ethanone; 2-benzofuranylethanone; (3-methyl-2-benzofuranyl)ethanone; benzophenone; 1,1,2,3,3,6-hexamethyl-5-indanylmethylketone, 6-tert-butyl-1,1-di-methyl-4-indanylmethylketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-aceto-naphthone;

of aromatic and araliphatic carboxylic acids and their esters such as e.g. benzoic acid; phenylacetic acid; methyl benzoate; ethyl benzoate; hexyl benzoate; benzyl benzoate; methyl phenyl acetate; ethyl phenyl acetate; geranyl phenyl acetate; phenylethyl phenyl acetate; methyl cinnamate; ethyl cinnamate; benzyl cinnamate; phenylethyl cinnamate; cinnamyl cinnamate; allyl phenoxy acetate; methyl salicylate; hexyl salicylate; cyclohexyl salicylate; cis-3-hexenyl salicylate; benzylsalicylate; phenylethyl salicylate; methyl 2,4-dihydroxy-3,6-dimethylbenzoate; ethyl-3-phenylglycidate; ethyl-3-methyl-3-phenylglycidate;

of nitrogen-containing aromatic compounds such as e.g. 2,4,6-trinitro-1,3-dimethyl-5-tert.butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methylanthranilate; methy-N-methylanthranilate; Schiff bases of methylanthranilate with 7-hydroxy-3,7-dimethyloctanal, 2-methyl-3-(4-tert.-butyl-phenyl)propanal or 2,4-dimethyl-3-cyclohexene carbaldehyde; 6-isopropyl quinoline; 6-isobutylquinoline; 6-sec.-butylquinoline; 2-(3-phenylpropyl)pyridine; indole; skatol; 2-methoxy-3-isopropylpyrazine; 2-isobutyl-3-methoxypyrazine;

of phenols, phenyl ethers and phenylesters such as estragol; anethol; eugenyl methylether; isoeugenol; isoeugenyl methylether; thymol; carvacrol; diphenylether; beta-naphthylmethylether; beta-naphthylethylether; beta-naphthyliso-butylether; 1,4-dimethoxybenzol; eugenylacetate; 2-methoxy-4-methylphenol; 2-ethoxy-5-(1-propenyl)phenol; p-kresylphenylacetate;

of heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones such as e.g. 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadeca-nolide; 9-hexadecene-1,16-olide; 10-oxa-1,16-hexadecanolide; 11-oxa-1,16-hexa-decanolide; 12-oxa-1,16-hexadecanolide; ethylene-1,12-dodecanedioate; ethylene-1,13-tridecanedioate; 2,3-dihydrocoumarin; octahydrocoumarin.

According to a preferred embodiment of the fragrance substance composition according to the invention, one or more compound(s) of formula (I) according to the invention is/are preferably combined with one or several, particularly preferably with two, three, four, five or more, additional fragrance substances.

Floral fragrance substances with which the one or more compound(s) of formula (I) according to the invention (in particular in fragrance substance compositions according to the invention) can be advantageously combined, are preferably selected from the group consisting of:

Hydroxycitronellal, methoxycitronellal, cyclamenaldehyde [2-methyl-3-(4-isopropylphenyl)propanal], 1-(4-isopropyl-cyclohexyl)ethanol (Mugetanol®), 4-tert.-butylmethyldihydrocinnamic aldehyde (Lilial®), cis-hexahydrocuminyl alcohol (Mayol®), 3-[4-(1,1-dimethylethyl)phenyl]propanal (Bourgenonal®), 2,2-dimethyl-3-(3-methylphenyl)propanol (Majantol®), 3-methyl-3-(3-methylbenzyl)-butan-2-ol, 2-isobutyl-4-methyltetrahydro-2H-pyran-4-ol (Florosa®), 2-methyl-3-(3,4-methylenedioxyphenyl)propanal (Heliofolal®), 4-(4-hydroxy-4-methylpentyl)-3-cyclohexene carbaldehyde (Lyral®), 4-(octahydro-4,7-methano-5H-inden-5-ylidene-butanal (Dupical®), vernaldehyde, 4-(4-methyl-3-penten-1-yl)-3-cyclohexene carbaldehyde (Vertomugal®), octahydro-5-(4-methoxybutylidene)-4,7-methano-1H-indene (Mugoflor®), 2,6-dimethyl-2-heptanol (Freesiol®); 1-ethyl-1-methyl-3-phenylpropanol (Phemec®), 2,2-dimethyl-3-phenyl-1-propanol (Muguet alcohol), profarnesol, dihydrofamesol, farnesol, nerolidol, hydroxycitronellaldimethylacetal, hexylbenzoate, geraniol, nerol, linalool, tetrahydrogeraniol, tetrahydrolinalool, ethyl-linalool, geranyltiglinate, phenethyl alcohol (2-phenylethyl alcohol), citronellol, rose oxide, 2-methyl-5-phenylpentanol (Rosaphene), 3-methyl-5-phenylpentanol (phenoxanol), methyldihydrojasmonate (Hedion®, Hedione® high cis), 2-heptylcyclopentanone (Projasmon P), cis-jasmone, dihydrojasmone, cinnamic alcohol (3-phenyl-2-propen-1-ol), dihydrocinnamic alcohol (3-phenylpropanol), 2-methyl-4-phenyl-1,3-dioxolane (Jacinthaflor®) and dihydromyrcenol (2,6-dimethyl-7-octen-2-ol).

Fruity fragrance substances with which the one or more compound(s) of formula (I) according to the invention can be advantageously combined, and which are therefore particularly preferred additional fragrance substances of a fragrance substance composition according to the invention, are preferably selected from the group consisting of:

2-Methyl-butyric acid ethyl ester, 4-(p-hydroxyphenyl)-2-butanone, ethyl-3-methyl-3-phenylglycidate, butyric acid isoamyl ester, acetic acid isoamyl ester, acetic acid n-butyl ester, butyric acid ethyl ester, 3-methyl-butyric acid ethyl ester, n-hexanoic acid ethyl ester, n-hexanoic acid allyl ester, ethyl-2-trans-4-cis-decadienoate; 1,1-dimethoxy-2,2,5-trimethyl-4-hexane, 2,6-dimethyl-5-hepten-1-al, gamma-undecalactone, gamma-nonalactone, hexanal, 3Z-hexenal, n-decanal, n-dodecanal, citral, vanillin, ethylvanillin, maltol, ethylmaltol and mixtures thereof.

Fragrance substance compositions according to the invention, which contain one or more compound(s) of formula (I), can be in liquid form, undiluted or diluted with a solvent. Preferred solvents are ethanol, isopropanol, diethylene glycol monoethyl ether, glycerol, propylene glycol, 1,2-butylene glycol, dipropylene glycol, diethyl phthalate, triethyl citrate, isopropyl myristate, triacetine and diacetine.

In addition, fragrance substance compositions according to the invention may be adsorbed to a carrier which ensures both a fine distribution of the fragrance substances in the product and a controlled release during application. Such carriers may be porous inorganic materials such as light sulphate, silica gels, zeolites, gypsums, clays, clay granules, gas concrete, etc. or organic materials such as wood, cellulose-based materials, sugars, dextrins (e.g. maltodextrin) or plastics such as PVC, polyvinyl acetates or polyurethanes. The combination of fragrance substance composition according to the invention and carrier is also to be understood as fragrance substance composition according to the invention or may be present as an product according to the invention (as described below).

Fragrance substance compositions or products (as described herein below) according to the invention may also be present in microencapsulated form, spray-dried form, as inclusion complexes or as extrusion products and—in case of a fragrance substance composition—may be added in this form to a product to be perfumed (as described herein below).

If applicable, the properties of such modified compositions or products can be further optimised by so-called "coating" with suitable materials in view of a more targeted release of fragrance, preferably using wax-like plastics such as e.g. polyvinyl alcohol. The resulting products in turn are products according to the invention.

Microencapsulation can, for example, be achieved by the so-called coacervation process with the aid of capsule materials, e.g. polyurethane-like substances or soft gelatine.

Spray-dried products are preferably produced by spray-drying an emulsion or dispersion containing the fragrance substance composition, whereby modified starches, proteins, dextrins and vegetable gums can be used as carriers.

Inclusion complexes can be prepared e.g. by incorporating dispersions of the fragrance substance composition and cyclodextrins or urea derivatives into a suitable solvent, e.g. water.

Extrusion products can be obtained e.g. by fusing the fragrance substance compositions with a suitable wax-like substance and by extrusion followed by solidification, if applicable in a suitable solvent, e.g. isopropanol.

Another aspect of the present invention relates to a perfumed product comprising a compound of formula (I) or a composition comprising one, two, three or more compounds of formula (I), or consisting of two, three or more compounds of formula (I), or a fragrance substance composition as defined herein.

Perfumed products according to the invention are e.g. perfume extracts, eau de parfums, eau de toilettes, aftershave lotions, eau de colognes, pre-shave products, splash colognes and perfumed refreshing wipes as well as perfuming of acidic, alkaline and neutral detergents, such as e.g. floor cleaners, window glass cleaners, dishwashing detergents, bathroom and sanitary cleaners, scouring milk, solid and liquid WC cleaners, powder and foam carpet cleaners, textile fresheners, ironing aids, liquid detergents, powder detergents, laundry pre-treatments such as bleaching agents, soaking agents and stain removers, fabric softeners, washing soaps, washing tablets, disinfectants, surface disinfectants and air fresheners in liquid or gel-like form or placed on a solid support, aerosol sprays, waxes and polishes such as furniture polishes, floor waxes, shoe polishes and body care products such as solid and liquid soaps, shower gels, shampoos, shaving soaps, shaving foams, bath oils, cosmetic emulsions of the oil-in-water, water-in-oil and water-in-oil-in-water type such as skin creams and lotions, facial creams and lotions, sun protection creams and lotions, after-sun creams and lotions, hand creams and lotions, foot creams and lotions, depilatory creams and lotions, after-shave creams and lotions, tanning creams and lotions, hair care products such as hair sprays, hair gels, solidifying hair lotions, hair conditioners, permanent and semi-permanent hair dyes, hair deformers such as cold waves and hair straighteners, hair toners, hair creams and lotions, deodorants and antiperspirants such as underarm sprays, roll-ons, deodorant sticks, deodorant creams, decorative cosmetic products such as eye shadows, nail varnishes, make-ups, lipsticks, mascara as well as candles, lamp oils, incense sticks, insecticides, repellents and fuels.

In a preferred embodiment of the perfumed product according to the invention, the one or more compound(s) of formula (I) is/are contained in a sensorially effective amount, preferably in an amount sufficient for a consumer to detect one or more olfactory notes selected from the group consisting of the notes green, fatty, ozonic, cyclamen-like, dusty, citrus, mandarin, aldehydic, citral, fresh, lily of the valley, bourgeonal, floral, cucumber, fruity and melon, preferably for a consumer to detect the olfactory note lily of the valley.

Preferably, the proportion of the total amount of one or more compound(s) of formula (I) contained in the perfumed product according to the invention, based on the total weight of the perfumed product, is between 0.05 and 10 wt. %, preferably between 0.1 and 5 wt. %, more preferably between 1 and 3 wt. %.

Another aspect of the present invention relates to a method for producing a perfumed product, preferably a perfumed product according to the invention as defined herein, comprising or consisting of the following steps:

(i) Providing a compound of formula (I) or a composition comprising one, two, three or more compounds of formula (I) or consisting of two, three or more compounds of formula (I) or a fragrance substance composition as defined herein, (ii) providing one or more further components of the perfumed product to be produced, and (iii) contacting or mixing the further components provided in step (ii) with a sensorially effective amount of the components provided in step (i).

Another aspect of the present invention relates to a method for perfuming hair, skin, textile fibres, surfaces and/or ambient air comprising or consisting of the following steps:

(a) Providing (i) a compound of formula (I) as defined herein and preferably also a surfactant or a surfactant mixture, or (ii) a composition comprising one, two, three or more compounds of formula (I), or consisting of two, three or more compounds of formula (I) as defined herein, preferably containing a surfactant or a surfactant mixture, or (iii) a fragrance substance composition as defined herein, preferably containing a surfactant or a surfactant mixture, or (iv) a perfumed product as defined herein, preferably containing a surfactant or a surfactant mixture, and (b) applying or introducing the (i) compound formula (I) and preferably also a surfactant or a surfactant mixture or the (ii) composition or the (iii) fragrance substance composition or the (iv) perfumed product to the hair or skin or fibres or surface to be perfumed, or into the ambient air to be perfumed, in a sensorially effective amount, preferably in an amount sufficient for a consumer to detect one or more olfactory notes selected from the group consisting of the notes green, fatty, ozonic, cyclamen-like, dusty, citrus, mandarin, aldehydic, citral, fresh, lily of the valley, bourgeonal, floral, cucumber, fruity and melon, preferably for a consumer to detect the olfactory note lily of the valley.

For preferred embodiments of the compounds of formula (I) (or of formula (Ia) or (Ib)) described herein, what has been stated in connection with the (fragrance substance) compositions, perfumed products, methods and uses according to the invention applies accordingly and vice versa.

In the following, the invention is explained in more detail using examples.

EXAMPLES

General Procedure 1: Grignard Addition

Under $N_2$ atmosphere, a solution of 2-(2-bromoethyl)-1,3-dioxolane (1.15 eq) in THF (0.5 vol w.r.t alkyl bromide) was slowly added to a suspension of Mg turnings (1.25 eq) in THF (5 vol w.r.t alkyl bromide). Mg was activated with a spatula of iodine. Grignard formation was maintained at a temperature of 37-40° C. for an hour, then a solution of ketone of formula (II) (1.0 eq) in THF (1 vol w.r.t to ketone) was then slowly added and reaction maintained at a temperature of 40° C. for 4 h. After completion of the reaction, the reaction mixture was quenched with ice cold saturated $NH_4Cl$ solution, compound extracted with MTBE (methyl-tert-butyl ether), washed with saturated $NaHCO_3$ and brine, and dried over $Na_2SO_4$, filtered and the solvents were removed in vacuo to yield the crude alcohol (compound of formula (III)).

General Procedure 2: Alcohol Elimination

To a solution of alcohol (compound of formula (III); 1.0 eq) in pyridine (2 vol w.r.t alcohol) at 0° C., $POCl_3$ (1.5 eq) was slowly added dropwise. After the addition, the suspension was stirred at 0° C. for 30 mins, then allowed to warm to room temperature and stirred at 50° C. until completion of the reaction. The reaction mixture was quenched with ice-water, extracted with ethyl acetate, 5% $H_2SO_4$, washed with saturated $NaHCO_3$ and brine, and dried over $Na_2SO_4$, filtered and the solvents were removed in vacuo to yield the compound of formula (IV).

General Procedure 3: Acetal Deprotection

The compound of formula (IV) (1.35 g; 1.0 eq) was dissolved in acetone (17 mL) and water (6 mL) and concentrated HCl (0.2 mL) was added, then the mixture was heated under reflux until completion of the reaction. At room temperature, the compound was extracted with MTBE, the organic layer was washed with saturated $NaHCO_3$ and brine, and dried over $Na_2SO_4$, filtered and the solvents removed in vacuo to yield the crude aldehyde (compound of formula (Ia)) as mixture of isomers.

Example 1

1-[2-(1,3-Dioxolan-2-yl)ethyl]-3-isopropyl-5-methyl-cyclohexanol

Following the general procedure 1, 2.0 g of 3-isopropyl-5-methy-cyclohexanone gave 2.3 g of 1-[2-(1,3-dioxolan-2-yl)ethyl]-3-isopropyl-5-methyl-cyclohexanol (70% yield).

1H NMR (400 MHz, $C_6D_6$) δ 4.86 (t, J=4.6 Hz; 1H), 3.57-3.52 (m, 2H), 3.40-3.35 (m, 2H), 1.96-1.88 (m, 2H), 1.82-1.70 (m, 1H), 1.63-1.56 (m, 4H), 1.56-1.47 (m, 2H), 1.42-1.30 (m, 1H), 0.86 (d, J=6.8 Hz, 3H), 0.86 (d, J=6.9 Hz, 3H), 0.85 (d, J=6.5 Hz, 3H), 0.78 (t, J=12.7 Hz, 1H), 0.65 (t, J=12.6 Hz, 1H), 0.43 (q, J=12.5 Hz, 1H).

$^{13}C$ NMR (101 MHz, $C_6D_6$) δ 105.30, 71.18, 64.89, 64.89, 46.11, 40.85, 38.83, 38.80, 38.36, 32.86, 28.22, 27.96, 22.84, 20.07, 19.76.

GC-MS: 237, 213, 195, 171, 155, 137, 102, 73, 58, 41, 29.

2-[2-(5-Isopropyl-3-methyl-cyclohexen-1-yl)ethyl]-1,3-dioxolane and 2-[2-(3-isopropyl-5-methyl-cyclohexen-1-yl)ethyl]-1,3-dioxolane Following general procedure 2, 2.9 g of 1-[2-(1,3-dioxolan-2-yl)ethyl]-3-isopropyl-5-methyl-cyclohexanol gave 2.9 g of a crude isomeric mixture of 2-[2-(5-isopropyl-3-methyl-cyclohexen-1-yl)ethyl]-1,3-dioxolane and 2-[2-(3-isopropyl-5-methyl-cyclohexen-1-yl)ethyl]-1,3-dioxolane (77% yield), which was carried forward to next step without further purification.

3-(5-Isopropyl-3-methyl-cyclohexen-1-yl)propanal and 3-(3-isopropyl-5-methyl-cyclohexen-1-yl)propanal Following general procedure 3, 2.5 g of an isomeric mixture of 2-[2-(5-isopropyl-3-methyl-cyclohexen-1-yl)ethyl]-1,3-dioxolane and 2-[2-(3-isopropyl-5-methyl-cyclohexen-1-yl)ethyl]-1,3-dioxolane gave 1.3 g of aldehyde as mixture of isomers (compounds of formula (I) or (Ia)) after column chromatography (3-5% EtOAc in cyclohexane, 66% yield).

1H NMR (600 MHz, $C_6D_6$) δ 9.37-9.34 (m, 2H), 5.20 (tt, J=2.3, 1.2 Hz, 1H), 5.14-5.10 (m, 1H), 2.07 (dtq, J=6.8, 4.9, 1.9 Hz, 1H), 2.04-1.93 (m, 9H), 1.68-1.60 (m, 3H), 1.55-1.45 (m, 4H), 1.41-1.31 (m, 2H), 1.31-1.24 (m, 1H), 0.93 (d, J=7.0 Hz, 3H), 0.90 (d, J=6.5 Hz, 3H), 0.88 (d, J=6.9 Hz, 3H), 0.87-0.84 (m, 9H), 0.76 (q, J=12.0 Hz, 1H), 0.66 (q, J=12.2, 10.8 Hz, 1H).

$^{13}$C NMR (151 MHz, $C_6D_6$) δ 200.59, 200.53, 136.42, 135.47, 128.32, 125.48, 43.07, 41.98, 40.98, 35.92, 34.37, 32.78, 32.54, 32.44, 32.07, 30.23, 29.96, 29.72, 22.58, 22.40, 19.92, 19.70, 19.64, 19.13.

GC-MS: 194, 176, 150, 133, 121, 107, 91, 55, 41, 29.

Odour: Green, fatty, ozonic, calamus, cyclamen-like, dusty.

Example 2

1-[2-(1,3-dioxolan-2-yl)ethyl]-5-isopropyl-3-methyl-cyclohex-2-en-1-ol

Following general procedure 1, 2.0 g of 5-isopropyl-3-methyl-cyclohex-2-en-1-one gave 3.0 g of 1-[2-(1,3-dioxolan-2-yl)ethyl]-5-isopropyl-3-methyl-cyclohex-2-en-1-ol (63% yield).

1H NMR (600 MHz, $C_6D_6$) δ 5.38 (dq, J=2.7, 1.4 Hz; 1H), 4.89 (t, J=4.7 Hz, 1H), 3.55-3.52 (m, 2H), 3.37-3.33 (m, 2H), 2.15-2.00 (m, 2H), 1.91-1.84 (m, 2H), 1.84-1.76 (m, 1H), 1.64 (dd, J=17.0, 5.3 Hz, 1H), 1.53 (s, 3H), 1.51-1.42 (m, 1H), 1.37-1.34 (m, 1H), 1.34-1.26 (m, J=6.6 Hz, 1H), 1.13 (t, J=12.7 Hz, 1H), 0.80 (d, J=6.7 Hz, 3H), 0.78 (d, J=6.7 Hz, 3H).

$^{13}$C NMR (151 MHz, $C_6D_6$) δ 134.35, 129.33, 105.29, 72.03, 64.86, 64.83, 40.91, 39.25, 35.81, 34.29, 32.54, 28.69, 23.49, 19.92, 19.53.

GC-MS: 253, 236, 211, 193, 153, 131, 105, 73, 55, 43, 29.

2-[2-(3-isopropyl-5-methyl-cyclohexa-1,5-dien-1-yl)ethyl]-1,3-dioxolane

Following general procedure 2, 3.0 g of 1-[2-(1,3-dioxolan-2-yl)ethyl]-5-isopropyl-3-methyl-cyclohex-2-en-1-ol gave 2.5 g of an isomeric mixture of 2-[2-(3-isopropyl-5-methyl-cyclohexa-1,5-dien-1-yl)ethyl]-1,3-dioxolane and its isomers.

GC-MS: 236, 207, 193, 174, 159, 131, 99, 73, 55, 29.

3-(5-Isopropyl-3-methyl-cyclohexa-1,3-dien-1-yl)propanal, 3-(3-isopropyl-5-methyl-cyclohexa-1,5-dien-1-yl)propanal, 3-(5-isopropyl-3-methylene-cyclohexen-1-yl)propanal and its isomers Following general procedure 3, 2.1 g of 2-[2-(3-isopropyl-5-methyl-cyclohexa-1,5-dien-1-yl)ethyl]-1,3-dioxolane and its isomers gave an isomeric mixture of aldehydes 3-(5-Isopropyl-3-methyl-cyclohexa-1,3-dien-1-yl)propanal, 3-(3-isopropyl-5-methyl-cyclohexa-1,5-dien-1-yl)propanal, 3-(5-isopropyl-3-methylene-cyclohexen-1-yl)propanal and its isomers (compounds of formula (I) or (Ia), 1.68 g, 25% yield). The crude product was purified and characterized by preparative liquid chromatography.

GC-MS: 192, 163, 121, 107, 93, 79, 41, 29.

Odour: Lily of the valley, aldehydic.

Example 3

1-[2-(1,3-Dioxolan-2-yl)ethyl]-3-isobutyl-5-methyl-cyclohexanol

Following general procedure 1, 2.0 g of 3-isobutyl-5-methy-cyclohexanone gave 2.6 g of crude product. After column chromatography (10-50% ethyl acetate in petroleum ether) 1.9 g of 1-[2-(1,3-dioxolan-2-yl)ethyl]-3-isobutyl-5-methyl-cyclohexanol were obtained.

$^1$H NMR (600 MHz, DMSO-$d_6$) δ 4.73 (t, J=4.9 Hz; 1H), 3.87-3.84 (m, 2H), 3.76-3.72 (m, 2H), 1.77-1.68 (m, 2H), 1.66-1.52 (m, 5H), 1.51-1.46 (m, 2H), 1.38-1.35 (m, 2H), 1.02-0.92 (m, 2H), 0.83 (dd, J=6.6, 3.1 Hz, 5H), 0.81 (d, J=6.6 Hz, 4H), 0.73 (t, J=12.6 Hz, 1H), 0.67 (t, J=12.5 Hz, 1H), 0.38 (q, J=12.1 Hz, 1H).

$^{13}$C NMR (151 MHz, DMSO-$d_6$) δ 104.72, 70.28, 64.62, 64.62, 46.96, 45.87, 43.90, 42.15, 38.70, 29.90, 27.97, 27.37, 24.75, 23.35, 23.23, 22.98.

GC-MS: 270, 251, 213, 195, 169, 151, 133, 102, 73, 58, 73, 58, 43, 29.

2-[2-(5-Isobutyl-3-methyl-cyclohexen-1-yl)ethyl]-1,3-dioxolane and 2-[2-(3-isobutyl-5-methyl-cyclohexen-1-yl)ethyl]-1,3-dioxolane Following general procedure 2, 1.9 g of 1-[2-(1,3-dioxolan-2-yl)ethyl]-3-isobutyl-5-methyl-cyclohexanol gave 1.7 g of crude product. After column chromatography (10% ethyl acetate in cyclohexane) 1.4 g of an isomeric mixture of the products 2-[2-(5-isobutyl-3-methyl-cyclohexen-1-yl)ethyl]-1,3-dioxolane and 2-[2-(3-isobutyl-5-methyl-cyclohexen-1-yl)ethyl]-1,3-dioxolane were obtained (77% yield).

$^1$H NMR (400 MHz, $C_6D_6$) δ 5.42-5.37 (m; 1H), 5.34 (tt, J=2.6, 1.2 Hz, 1H), 4.90 (t, J=4.7 Hz, 2H), 3.58-3.53 (m, 4H), 3.41-3.37 (m, 4H), 2.26 (t, J=8.2 Hz, 4H), 2.21-2.12 (m, 2H), 2.00-1.92 (m, 4H), 1.94-1.88 (m, 1H), 1.89-1.82 (m, 1H), 1.75-1.58 (m, 6H), 1.60-1.45 (m, 2H), 1.20-1.07 (m, 2H), 1.07 (t, J=7.0 Hz, 2H), 0.96 (d, J=7.0 Hz, 3H), 0.90 (d, J=6.8 Hz, 3H), 0.87 (d, J=6.7 Hz, 6H), 0.86 (d, J=6.6 Hz, 6H), 0.68 (q, J=12.2, 10.7 Hz, 1H), 0.68 (q, J=12.2, 10.7 Hz, 1H).

$^{13}$C NMR (101 MHz, $C_6D_6$) δ 136.60, 136.42, 127.87, 126.49, 104.70, 104. 55, 64.89, 64.89, 64.89, 64.89, 47.10, 46.91, 39.62, 39.31, 37.93, 36.03, 34.56, 33.04, 33.01, 32.52, 32.40, 32.37, 31.84, 29.77, 25.10, 25.01, 23.39, 23.31, 22.85, 22.62, 22.60, 22.48.

GC-MS: 252, 224, 209, 190, 164, 133, 107, 99, 86, 73, 55, 41, 29.

3-(5-Isobutyl-3-methyl-cyclohexen-1-yl)propanal and 3-(3-isobutyl-5-methyl-cyclohexen-1-yl)propanal Following general procedure 3, 1.4 g of 2-[2-(5-isobutyl-3-methyl-cyclohexen-1-yl)ethyl]-1,3-dioxolane and 2-[2-(3-isobutyl-5-methyl-cyclohexen-1-yl)ethyl]-1,3-dioxolane gave, after column chromatography (3-5% ethyl acetate in cyclohexane), 1.03 g of isomeric mixture of aldehydes 3-(3-isobutyl-5-methyl-cyclohexen-1-yl)propanal and 3-(5-isobutyl-3-methyl-cyclohexen-1-yl)propanal (compounds of formula (I) or (Ia)).

$^1$H NMR (400 MHz, $C_6D_6$) δ 9.37-9.35 (m, 2H), 5.21-5.16 (m, 1H), 5.16-5.10 (m, 1H), 2.20-2.07 (m, 2H), 2.05-1.92 (m, 8H), 1.75-1.69 (m, 1H), 1.71-1.59 (m, 5H), 1.59-1.47 (m, 2H), 1.42-1.29 (m, 2H), 1.15 (dt, J=13.7, 7.7, 6.9 Hz, 1H), 1.10-1.04 (m, 1H), 1.06 (t, J=7.0 Hz, 2H), 0.93 (d, J=7.0 Hz, 3H), 0.91-0.86 (m, 15H), 0.62 (q, J=12.4, 10.7 Hz, 2H).

$^{13}$C NMR (101 MHz, $C_6D_6$) δ 200.55, 200.51, 135.45, 135.27, 128.33, 127.05, 47.02, 46.79, 42.00, 41.97, 39.38, 39.07, 37.78, 35.93, 34.48, 32.25, 31.73, 30.09, 29.95, 29.62, 25.11, 25.05, 23.39, 23.25, 22.87, 22.55, 22.52, 22.35.

GC-MS: 208, 190, 164, 149, 133, 121, 107, 95, 79, 67, 55, 41, 29.

Odour: Citrus, mandarin, aldehydic, citral, pleasantly fresh.

Example 4

1-[2-(1,3-dioxolan-2-yl)ethyl]-5-isobutyl-3-methyl-cyclohex-2-en-1-ol

Following general procedure 1, 2.0 g of 5-isobutyl-3-methyl-cyclohex-2-en-1-one, after column chromatography (10-50% ethyl acetate in cyclohexane), gave 2.9 g of 1-[2-(1,3-dioxolan-2-yl)ethyl]-5-isobutyl-3-methyl-cyclohex-2-en-1-ol.

$^1$H NMR (400 MHz, $CDCl_3$) δ 5.33 (d, J=1.4 Hz, 1H), 4.90 (t, J=4.6 Hz, 1H), 4.06-3.93 (m, 2H), 3.93-3.80 (m, 2H), 2.05-1.68 (m, 8H), 1.66 (d, J=1.4 Hz, 3H), 1.64-1.43 (m, 2H), 1.29-1.18 (m, 1H), 1.15 (t, J=7.1 Hz, 2H), 0.88 (dd, J=6.6 Hz, 6H).

$^{13}$C NMR (101 MHz, $CDCl_3$) δ 135.51, 127.70, 104.79, 71.89, 64.92, 64.92, 46.17, 43.65, 37.49, 35.47, 30.37, 27.93, 24.77, 23.41, 22.97, 22.69.

GC-MS: 250, 221, 207, 188, 162, 131, 99, 73, 55.

2-[2-(3-isobutyl-5-methyl-cyclohexa-1,5-dien-1-yl)ethyl]-1,3-dioxolane, 2-[2-(5-isobutyl-3-methyl-cyclohexa-1,3-dien-1-yl)ethyl]-1,3-dioxolane, 2-[(2Z)-2-(5-isobutyl-3-methyl-cyclohex-2-en-1-ylidene)ethyl]-1,3-dioxolane, 2-[(2E)-2-(5-isobutyl-3-methyl-cyclohex-2-en-1-ylidene)ethyl]-1,3-dioxolane and 2-[2-(5-isobutyl-3-methylene-cyclohexen-1-yl)ethyl]-1,3-dioxolane Following general procedure 2, 2.9 g of 1-[2-(1,3-dioxolan-2-yl)ethyl]-5-isobutyl-3-methyl-cyclohex-2-en-1-ol gave 1.96 g of an isomeric mixture of 2-[2-(3-isobutyl-5-methyl-cyclohexa-1,5-dien-1-yl)ethyl]-1,3-dioxolane and its isomers.

$^1$H NMR (400 MHz, $CDCl_3$) δ 6.31 (s, 1H), 6.08 (s, 1H), 5.98 (s, 1H), 5.61 (s, 1H), 5.62 (s, 1H), 5.53 (t, J=7.5 Hz, 1H), 5.42 (t, J=7.5 Hz, 1H), 5.37 (m, 1H), 5.33 (dt, J=3.5 Hz, 1.6 Hz, 1H), 4.95 (t, J=4.9 Hz, 1H), 4.93 (t, J=4.8 Hz, 1H), 4.88 (t, J=4.8 Hz, 1H), 4.85 (t, J=4.8 Hz, 1H), 4.84-4.80 (m, 2H), 4.78 (t, J=4.8 Hz, 1H), 3.56-3.49 (m, 10H), 3.47-3.32 (m, 10H), 2.36 (t, J=7.7 Hz, 2H), 2.34 (mc, 3H), 2.31 (mc, 2H), 2.26 (t, J=7.8 Hz, 2H), 2.09 (dd, J=16.6 Hz, 7.5 Hz, 1H), 2.02 (dd, J=16.9 Hz, 8.3 Hz, 1H), 1.95 (mc, 4H), 1.91 (mc, 6H), 1.75 (mc, 4H), 1.71 (t, J=1.8 Hz, 3H), 1.68 (mc, 5H), 1.59 (mc, 7H), 1.32 (mc, 4H), 1.14 (mc, 2H), 1.04 (mc, 6H), 0.87-0.72 (m, 42H).

$^{13}$C NMR (101 MHz, $CDCl_3$) δ 144.1, 141.2, 138.6, 138.3, 137.9, 136.9, 135.5, 135.5, 135.1, 131.6, 127.3, 125.3, 123.9, 123.1, 122.8, 122.3, 120.8, 118.5, 116.8, 109.3, 104.8, 104.7, 104.6, 104.5, 104.4, 64.9, 64.9, 64.9, 64.9, 64.8, 64.8, 64.8, 64.8, 64.8, 64.8, 46.0, 45.9, 45.6, 44.7, 44.4, 39.2, 38.3, 37.7, 37.6, 35.9, 35.6, 34.4, 33.9, 33.7, 33.4, 32.8, 32.6, 35.5, 32.4, 32.3, 32.1, 32.02, 32.02, 32.02, 32.02, 31.9, 31.8, 31.7, 30.6, 25.4, 25.3, 25.2, 25.2, 24.5, 24.2, 23.8, 23.5, 23.2, 23.1, 23.0, 22.9, 22.9, 22.9, 22.8, 21.7.

3-(5-isobutyl-3-methyl-cyclohexa-1,3-dien-1-yl)propanal, 3-(3-isobutyl-5-methyl-cyclohexa-1,5-dien-1-yl)propanal; 3-(5-isobutyl-3-methylenecyclohex-1-en-1-yl)propanal and 3-(5-isobutyl-3-methyl-cyclohex-2-en-1-ylidene)propanal (1:1:1:1 mixture)

Following general procedure 3, 1.9 g of the mixture of acetals gave 0.58 g of a crude mixture of aldehydes (compounds of formula (I) or (Ia)). Using preparative liquid chromatography and sniff gas chromatography, the compounds of formula (I) or (Ia) were isolated and characterized.

GC-MS: 206, 177, 121, 93, 79, 55, 41.

Odour: Aldehyde, watery, cucumber, green

Example 5

1-[2-(1,3-dioxolan-2-yl)ethyl]-4-isopropyl-cyclohexanol

Following general procedure 1, 2.0 g of 4-isopropylcyclohexanone gave 2.9 g of 1-[2-(1,3-dioxolan-2-yl)ethyl]-4-isopropyl-cyclohexanol (53% yield).

2-[2-(4-isopropylcyclohexen-1-yl)ethyl]-1,3-dioxolane

Following general procedure 2, 2.8 g of 1-[2-(1,3-dioxolan-2-yl)ethyl]-4-isopropyl-cyclohexanol gave 1.98 g of 2-[2-(4-isopropylcyclohexen-1-yl)ethyl]-1,3-dioxolane.

$^1$H NMR (400 MHz, $CDCl_3$) δ 5.42 (mc, 1H), 4.86 (t, J=4.86 Hz, 1H), 3.97 (mc, 2H), 3.85 (mc, 2H), 2.06 (mc, 2H), 1.97 (mc, 2H), 1.75 (mc, 5H), 1.44 (mc, 1H), 1.21 (mc, 2H), 0.89 (d, J=6.6 Hz, 3H), 0.87 (d, J=6.7 Hz, 3H).

$^{13}$C NMR (101 MHz, $CDCl_3$) δ 136.75, 120.90, 104.46, 64.87, 64.85, 40.16, 32.29, 32.18, 31.83, 29.14, 28.93, 26.47, 19.99, 19.68.

GC-MS: 224, 209, 195, 179, 162, 147, 133, 119, 99, 86, 73, 55, 41, 29.

3-(4-isopropylcyclohexen-1-yl)propanal

Following general procedure 3, 1.7 g of 2-[2-(4-isopropylcyclohexen-1-yl)ethyl]-1,3-dioxolane gave 1.3 g of 3-(4-isopropylcyclohexen-1-yl)propanal (compound of formula (Ia)).

GC-MS: 180, 162, 136, 119, 93, 79, 67, 55, 41, 29.

$^1$H NMR (400 MHz, $CDCl_3$): δ=0.87 (d, J=6.8 Hz, 3H), 0.88 (d, J=0.88 Hz, 3H), 1.16-1.28 (m, 2H), 1.42-1.50 (m, 1H), 1.66-1.80 (m, 2H), 1.94-2.06 (m, 3H), 2.28 (t, J=7.5 Hz, 2H), 2.49-2.54 (m, 2H), 5.39-5.43 (m, 1H), 9.75 (t, J=1.9 Hz, 1H).

$^{13}$C NMR (100 MHz, $CDCl_3$): δ 19.6, 19.9, 26.3, 28.8, 29.2, 29.7, 32.2, 40.0, 41.9, 121.8, 135.5, 202.8.

Odour: Strong, Lily of the valley, aldehydic.

Example 6

Synthesis of 3-(5-isopropyl-2-methylene-cyclohexyl)propanal a) 2-[2-(1,3-Dioxolan-2-yl)ethyl]-4-isopropyl-cyclohexanone To a suspension of NaH (2.7 g, 2.0 eq) in N,N-diethylformamide (25 mL), 4-isopropylcyclohexanone (5.0 g, 1.0 eq) was added at a temperature between 0-5° C. and maintained at this temperature for about 45 min. Below 10° C., 2-(2-bromoethyl)-1,3-dioxolane (7.8 g; 1.2 eq) was added dropwise. After addition, the reaction mixture was maintained at room temperature until completion of the reaction (~3-4 h). The reaction was quenched with ice-water, the mixture washed with 10% $H_2SO_4$, water and then the compound was extracted using MTBE. The organic phase was washed with saturated $NaHCO_3$, washed with water until the pH of the aqueous layer was neutral and then dried over $Na_2SO_4$, filtered and the solvents were removed in vacuo to yield the crude product (7.73 g). Purification of the crude product by Kugelrohr distillation (T=150° C., p=0.1 mbar) gave the title compound of formula (VI) (6.2 g, 72%).

$^1$H NMR (600 MHz, $C_6D_6$) δ 4.86 (td, J=4.8, 0.9 Hz, 1H), 3.59-3.56 (m, 2H), 3.40 (dt, J=5.5, 1.8 Hz, 2H), 2.26-2.22 (m, 1H), 2.21-2.12 (m, 1H), 2.01-1.95 (m, 1H), 1.94-1.89 (m, 1H), 1.89-1.83 (m, 1H), 1.83-1.77 (m, 1H), 1.77-1.71 (m, 1H), 1.46-1.39 (m, 1H), 1.38-1.27 (m, 2H), 1.24-1.18 (m, 1H), 1.17-1.11 (m, 1H), 0.85-0.83 (m, 1H), 0.70 (d, J=6.8 Hz, 3H), 0.68 (d, J=6.8 Hz, 3H).

$^{13}$C NMR (151 MHz, $C_6D_6$) δ 210.43, 105.13, 64.85, 64.85, 49.31, 43.07, 41.57, 37.29, 32.15, 32.10, 30.41, 24.46, 20.02, 19.74.

GC-MS: 240, 222, 197, 178, 135, 99, 73, 55, 45, 29.

b) 2-[2-(5-Isopropyl-2-methylene-cyclohexyl)ethyl]-1,3-dioxolane

Under $N_2$ atmosphere, potassium tert-butoxide (1.07 g, 1.25 eq) was added to a suspension of methyl(triphenyl) phosphonium bromide (2.97 g, 1.0 eq) in THF (20 mL) at a temperature between 0-5° C. and the mixture was maintained at room temperature for 30 min. To this mixture, a solution of 2-[2-(1,3-dioxolan-2-yl)ethyl]-4-isopropyl-cyclohexanone (2.0 g, 1.0 eq) in THF (10 mL) was added dropwise and refluxed until completion of the reaction (~3 h). The reaction was quenched with ice water, and the compound was extracted using MTBE. The organic phase was washed with water until the pH of the aqueous layer was neutral and then dried over $Na_2SO_4$, filtered and the solvents were removed in vacuo to yield the crude product (4.78 g, contaminated with Wittig salt). Purification of the crude product by Kugelrohr distillation (T=155° C., p=0.3 mbar) gave the title compound of formula (VII) (1.2 g, 60%).

$^1$H NMR (600 MHz, $C_6D_6$) δ 4.88-4.85 (m, 1H), 4.81 (dq, J=7.6, 1.7 Hz, 2H), 3.58-3.55 (m, 2H), 3.41-3.38 (m, 2H), 2.32 (ddd, J=12.8, 4.0, 2.7 Hz, 1H), 1.95-1.87 (m, 4H), 1.87-1.81 (m, 1H), 1.80-1.76 (m, 1H), 1.68-1.63 (m, 1H), 1.58-1.51 (m, 1H), 1.32-1.28 (m, 1H), 1.17-1.10 (m, 1H), 1.05-0.97 (m, 1H), 0.81 (d, J=5.8 Hz, 3H), 0.79 (d, J=5.7 Hz, 3H), 0.74 (q, J=12.1 Hz, 1H).

$^{13}$C NMR (151 MHz, $C_6D_6$) δ 152.94, 105.18, 104.69, 64.89, 64.88, 44.35, 42.58, 38.39, 37.33, 32.85, 32.29, 31.99, 27.19, 20.11, 19.80.

GC-MS: 238, 209, 195, 176, 150, 133, 99, 73, 57, 45, 29.

c) 3-(5-Isopropyl-2-methylene-cyclohexyl)propanal

The reaction product of step b) above was deprotected to the product 3-(5-isopropyl-2-methylene-cyclohexyl)propanal (compound of formula (I) or (Ib)) following a procedure analogous to general procedure 3 (acetal deprotection) in 60% yield.

GC-MS: 194, 176, 161, 133, 91, 79, 67, 55, 41.

Odour: Lily of the valley, aldehydic, floral.

The invention claimed is:

1. A compound of formula (I)

(I)

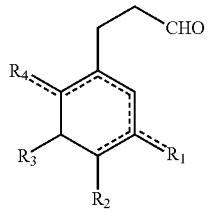

wherein $R_1$ represents H, methyl, isopropyl, or $=CH_2$, $R_2$ represents H, $R_3$ represents H, isopropyl, or isobutyl, $R_4$ represents H or $=CH_2$, and dashed lines represent a possible double bond, provided the compound comprises one or two double bonds along the dashed lines.

2. The compound of claim 1 selected from 3-(5-isopropyl-2-methylene-cyclohexyl)-propanal, 3-(5-isopropyl-3-methyl-cyclohexen-1-yl) propanal, 3-(3-isopropyl-5-methyl-cyclohexen-1-yl) propanal, 3-(5-isobutyl-3-methyl-cyclohexen-1-yl) propanal, 3-(3-isobutyl-5-methyl-cyclohexen-1-yl) propanal, 3-(3-isobutyl-5-methyl-cyclohexa-1,5-dien-1-yl) propanal, 3-(5-isobutyl-3-methyl-cyclohexa-1,3-dien-1-yl) propanal, 3-(5-isobutyl-3-methylenecyclohex-1-en-1-yl) propanal, 3-(5-isopropyl-3-methyl-cyclohexa-1,3-dien-1-yl) propanal, 3-(3-isopropyl-5-methyl-cyclohexa-1,5-dien-1-yl) propanal, and 3-(5-isopropyl-3-methylene-cyclohexen-1-yl) propanal.

3. A composition comprising one or more of the compounds of claim 1.

4. A fragrance substance composition comprising one or more of the compounds of claim 1 and one or more additional fragrance substances.

5. A perfumed product comprising a sensorially effective amount of one or more of the compounds of claim 1.

6. The perfumed product of claim 5, wherein the one or more compounds are in an amount to provide the product with one or more olfactory notes selected from a green note, a fatty note, an ozonic note, a cyclamen-like note, a dusty note, a citrus note, a mandarin note, an aldehydic note, a citral note, a fresh note, a lily of the valley note, a bourgeonal note, a floral note, a cucumber note, a fruity note, and a melon note.

7. The perfumed product of claim 6, wherein the one or more compounds provide the product with the lily of the valley note.

8. A method for producing a perfumed product comprising:

(i) providing one or more compounds of claim 1;

(ii) providing one or more further components of the perfumed product; and (iii) contacting or mixing the further components of (ii) with a sensorially effective amount of the one or more compounds of (i).

9. A method for perfuming hair, skin, textile fibers, surfaces, ambient air, or a combination thereof comprising:

(a) providing one or more compounds of claim 1, a composition comprising the one or more compounds, or a perfumed product comprising the one or more compounds; and (b) imparting the one or more compounds, the composition, or the perfumed product to the hair, skin, textile fibers, surfaces, ambient air, or a combination thereof in a sensorially effective amount.

10. The method of claim 9, wherein the method imparts one or more olfactory notes selected from a green note, a fatty note, an ozonic note, a cyclamen-like note, a dusty note, a citrus note, a mandarin note, an aldehydic note, a citral note, a fresh note, a lily of the valley note, a bourgeonal note, a floral note, a cucumber note, a fruity note, and a melon note.

11. The method of claim 10, wherein the method imparts the lily of the valley note.

12. A method for producing the compound of claim 1 comprising one or more of the following reaction steps:

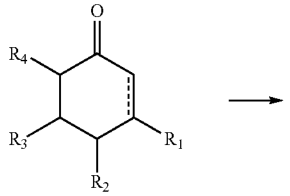

(II)
$R_1$ = H or methyl
$R_2$ = H or isopropyl
$R_3$ = H, isopropyl or isobutyl
$R_4$ = H

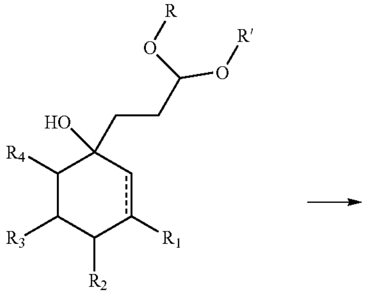

(III)
$R_1$ = H or methyl
$R_2$ = H or isopropyl
$R_3$ = H, isopropyl or isobutyl
$R_4$ = H
R, R′ = independently alkyl or are connected via an alkyl group

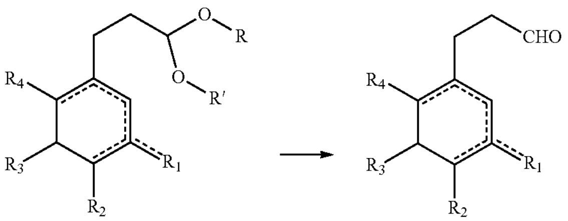

(IV)
$R_1$ = H, or methyl or = $CH_2$
$R_2$ = H or isopropyl
$R_3$ = H, isopropyl or isobutyl
$R_4$ = H
R, R′ = independently alkyl or are connected via an alkyl group (Ia)
$R_1$ = H, or methyl or = $CH_2$
$R_2$ = H or isopropyl
$R_3$ = H, isopropyl or isobutyl
$R_4$ = H wherein dashed lines represent a possible double bond, provided the compound of formula (IV) comprises one or two double bonds along the dashed lines.

13. The method of claim 12, wherein the compound of formula (Ia) is selected from 3-(5-isopropyl-3-methyl-cyclohexen-1-yl) propanal, 3-(3-isopropyl-5-methyl-cyclohexen-1-yl) propanal, 3-(5-isobutyl-3-methyl-cyclohexen-1-yl) propanal, 3-(3-isobutyl-5-methyl-cyclohexen-1-yl) propanal, 3-(3-isobutyl-5-methyl-cyclohexa-1,5-dien-1-yl) propanal, 3-(5-isobutyl-3-methyl-cyclohexa-1,3-dien-1-yl) propanal, 3-(5-isobutyl-3-methylenecyclohex-1-en-1-yl) propanal, 3-(5-isopropyl-3-methyl-cyclohexa-1,3-dien-1-yl) propanal, 3-(3-isopropyl-5-methyl-cyclohexa-1,5-dien-1-yl) propanal, 3-(5-isopropyl-3-methylene-cyclohexen-1-yl) propanal, and 3-(4-isopropylcyclohexen-1-yl) propanal.

14. A method for producing a compound of formula (I)

(I)

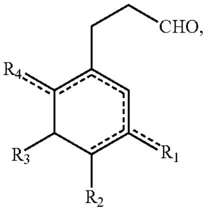

wherein $R_1$ represents isopropyl, $R_2$ represents H, $R_3$ represents H, $R_4$ represents $=CH_2$, and dashed lines represent a possible double bond, provided the compound comprises one or two double bonds along the dashed lines, and wherein the compound is designated as a compound of formula (Ib), the method comprising one or more of the following reaction steps:

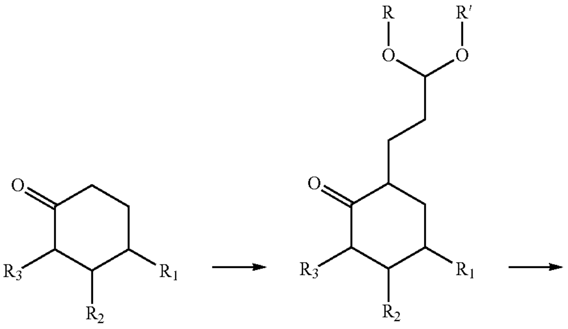

(V)
$R_1$ = isopropyl
$R_2$ = H
$R_3$ = H (VI)
$R_1$ = isopropyl
$R_2$ = H
$R_3$ = H
R, R′ = independently alkyl or are connected via an alkyl group -continued
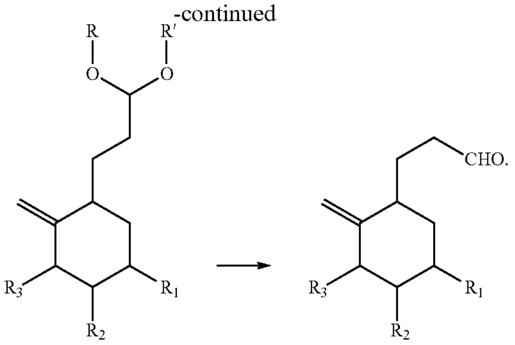
(VII)
$R_1$ = isopropyl
$R_2$ = H
$R_3$ = H
R, R′ = independently alkyl or are connected via an alkyl group
(Ib)
$R_1$ = isopropyl
$R_2$ = H
$R_3$ = H
15. The method of claim 14, wherein the compound of formula (I) or (Ib) is 3-(5-isopropyl-2-methylene-cyclohexyl)propanal.
* * * * *